(12) United States Patent
Kohlstruk et al.

(10) Patent No.: US 7,329,776 B2
(45) Date of Patent: *Feb. 12, 2008

(54) MULTISTAGE CONTINUOUS PREPARATION OF CYCLOALIPHATIC DIISOCYANATES

(75) Inventors: Stephan Kohlstruk, Duelmen (DE); Manfred Kreczinski, Herne (DE); Rainer Elm, Marl (DE); Hans-Werner Michalczak, Herne (DE)

(73) Assignee: Degussa AG, Düsseldorf (DE)

( * ) Notice: Subject to any disclaimer, the term of this patent is extended or adjusted under 35 U.S.C. 154(b) by 482 days.

This patent is subject to a terminal disclaimer.

(21) Appl. No.: 10/921,934

(22) Filed: Aug. 20, 2004

(65) Prior Publication Data

US 2005/0043562 A1     Feb. 24, 2005

(30) Foreign Application Priority Data

Aug. 22, 2003  (DE) ................. 103 38 511

(51) Int. Cl.
   *C07C 263/00*   (2006.01)
(52) U.S. Cl. .................................... 560/345
(58) Field of Classification Search ................ 560/330
   See application file for complete search history.

(56) References Cited

U.S. PATENT DOCUMENTS

| | | | |
|---|---|---|---|
| 2,692,275 A | 10/1954 | Bortnick et al. | |
| 3,919,279 A | 11/1975 | Rosenthal et al. | |
| 4,081,472 A * | 3/1978 | Tsumura et al. | 560/345 |
| 4,268,683 A | 5/1981 | Gurgiolo | |
| 4,386,033 A | 5/1983 | Koenig et al. | |
| 4,388,246 A | 6/1983 | Sundermann et al. | |
| 4,462,550 A | 7/1984 | Tyler | |
| 4,530,796 A | 7/1985 | Mattner et al. | |
| 4,596,678 A | 6/1986 | Merger et al. | |
| 4,596,679 A | 6/1986 | Hellbach et al. | |
| 4,713,476 A | 12/1987 | Merger et al. | |
| 4,851,565 A | 7/1989 | Merger et al. | |
| 5,087,739 A | 2/1992 | Bohmholdt et al. | |
| 5,360,931 A | 11/1994 | Bohmholdt et al. | |
| 5,386,053 A * | 1/1995 | Otterbach et al. | 560/344 |
| 5,453,536 A | 9/1995 | Dai et al. | |
| 5,502,244 A | 3/1996 | Okawa et al. | |
| 5,616,784 A | 4/1997 | Schwarz et al. | |
| 5,646,328 A | 7/1997 | Deibele et al. | |
| 5,744,633 A | 4/1998 | Wilmes et al. | |
| 5,962,728 A | 10/1999 | Mason et al. | |
| 6,204,409 B1 | 3/2001 | Aso et al. | |
| 2005/0043562 A1 | 2/2005 | Kohlstruk et al. | |

FOREIGN PATENT DOCUMENTS

| | | |
|---|---|---|
| DE | 1 022 222 | 1/1958 |
| DE | 196 27 552 A1 | 1/1998 |
| DE | 101 27 273 | 12/2002 |
| EP | 0 355 443 A2 | 2/1990 |
| EP | 0 566 925 A2 | 10/1993 |

OTHER PUBLICATIONS

U.S. Appl. No. 11/100,603, filed Apr. 7, 2005, Kohlstruk et al.
U.S. Appl. No. 11/101,428, filed Apr. 8, 2005, Kohlstruk et al.
U.S. Appl. No. 11/185,776, filed Jul. 21, 2005, Kohlstruk et al.
U.S. Appl. No. 10/917,463, filed Aug. 13, 2004, Kohlstruk et al.
U.S. Appl. No. 10/922,910, filed Aug. 23, 2004, Kohlstruk et al.
U.S. Appl. No. 10/921,934, filed Aug. 20, 2004, Kohlstruk et al.

* cited by examiner

*Primary Examiner*—Yvonne Eyler
*Assistant Examiner*—Kellette Gale
(74) *Attorney, Agent, or Firm*—Oblon, Spivak, McClelland, Maier & Neustadt, P.C.

(57) ABSTRACT

A multistage process for continuous and phosgene-free preparation of cycloaliphatic diisocyanates.

119 Claims, No Drawings

MULTISTAGE CONTINUOUS PREPARATION OF CYCLOALIPHATIC DIISOCYANATES

BACKGROUND OF THE INVENTION

The invention relates to a multistage process for continuous and phosgene-free preparation of cycloaliphatic diisocyanates, diisocyanates produced by the process and use of the diisocyanates for forming polymers or coatings.

1. Field of the Invention

The synthesis of isocyanates may be via a series of different routes. The phosgene route is used for the industrial scale preparation of isocyanates and is the oldest and still predominates today. This process is based on the reaction of amines with phosgene. A disadvantage of the phosgene process is that phosgene must be used which, as a consequence of its toxicity and corrosivity, places particularly high safety and equipment requirements on its handling on an industrial scale.

2. Description of the Related Art

There are several processes for preparing isocyanates which avoid the use of phosgene on an industrial scale. The term phosgene-free process is frequently used in connection with the conversion of amines to isocyanates using alternative carbonylating agents such as, for example, urea or dialkyl carbonate (U.S. Pat. Nos. 4,713,476; 5,087,739; 4,268,683; 6,204,409).

The urea route is based on the urea-mediated conversion of diamines to diisocyanates via a two-stage process. In a first step, a diamine is reacted with alcohol in the presence of urea or urea equivalents (for example alkyl carbonates, alkyl carbamates) to give a diurethane which typically passes through an intermediate purification stage and is then thermally cleaved in a second step to form a diisocyanate and alcohol (U.S. Pat. Nos. 5,087,739; 4,713,476; 5,386,053). Alternatively, the actual urethane formation may also be preceded by the separate preparation of a diurea by selectively reacting the diamine with urea (U.S. Pat. No. 5,360,931). Also conceivable is a two-stage sequence consisting of a partial reaction of urea with alcohol in the first step and subsequent metering in and urethanization of the diamine in the second step (U.S. Pat. No. 5,744,633).

The thermal cleavage of urethanes to the corresponding isocyanates and alcohols has been known for some time and can be carried out either in the gas phase at high temperatures or at relatively low temperatures in the liquid phase. However, a problem with both procedures is that the thermal stress inevitably also causes undesired side reactions to take place which reduce the yield and lead to the formation of resinifying by-products which considerably disrupt the course of an industrial process as a result of deposits and blockages which may form in reactors and workup apparatus.

There has been no shortage of suggestions of chemical and process technology measures to achieve yield improvements and limit the undesired by-product formation. For instance, a series of documents describes the use of catalysts which accelerate the cleavage reaction of the urethanes (DE 10 22 222, U.S. Pat. Nos. 3,919,279, 4,081,472). Indeed, it is entirely possible in the presence of suitable catalysts, of which a multitude of basic, acidic and also organometallic compounds are known, to increase the isocyanate yield in comparison to the uncatalyzed variant. However, the formation of undesired by-products can not be prevented by the presence of a catalyst. The same applies to the additional use of inert solvents in order to ensure uniform distribution of the heat supplied and of the catalyst in the reaction medium, as recommended in U.S. Pat Nos. 3,919,279 and 4,081,472. However, the process which utilizes solvents boiling under reflux results in a reduction in the space-time yield of isocyanates and is additionally hindered with the disadvantage of additional high energy demands.

Examples for thermally catalyzed cleavage of monourethanes disclose the partial discharge of the reaction mixture to remove resinifying by-products formed in the course of the urethane cleavage are described in U.S. Pat. No. 4,386,033. This procedure serves to prevent deposits and blockages in reactors and workup units. There is however no disclosure which points to a yield-increasing utilization of the partial discharge. U.S. Pat. No. 4,388,246 describes a similar solution in which thermolysis is carried out in the presence of solvents whose purpose is apparently to better absorb the non-volatile by-products. Here also, the partial discharge is not utilized for the purposes of yield optimization.

U.S. Pat. No. 5,087,739 discloses that a yield increase can be achieved when higher molecular weight by-products which are formed in the cleavage reactor during the cleavage of diurethanes and may or may not be utilized to ensure a disruption-free and selective reaction, are discharged substantially continuously out of the reactor and subsequently converted for the most part in the presence of alcohol and then recycled into the diurethane preparation. The procedure is associated with high energy demands since nonutilizable by-products are removed from the effluent of the diurethane preparation by distillation, and all of the diurethane has to be evaporated. In contrast to U.S. Pat. No. 5,087,739, the urethanization effluent in the process of U.S. Pat. No. 5,386,053 is divided into two substreams of which only one is freed by distillation of its high-boiling, nonutilizable by-products, before the combined diurethane streams are fed to the deblocking reaction in the cleavage reactor. In addition, the continuous cleavage reactor discharge in U.S. Pat. No. 5,386,053 is recycled directly, i.e., without a reurethanization step, into the diurethane synthesis.

The method of U.S. Pat. No. 5,386,053 has the consequence that some of the high boiler components from the diurethane synthesis, via the deblocking or cleavage stage, get back into the diurethane preparation and into the diurethane purification procedure.

SUMMARY OF THE INVENTION

It has been found that, surprisingly, when cycloaliphatic diamines are used to form cycloaliphatic diisocyanates, it is advantageous to free the cycloaliphatic diurethanes of low and medium boilers after their synthesis by reacting the cycloaliphatic diamines with alcohol and urea and/or urea derivatives, to thermally cleave the cycloaliphatic diurethanes purified in this way to release the desired cycloaliphatic diisocyanate, to continuously discharge a portion of the cleavage residue from the cleavage apparatus and remove from it high boiler components, and to reurethanize with alcohol the discharge which has been purified in this way and to recycle it into the process. It has been found that this method firstly realizes a comparatively low steady-state concentration of high boiler components over the entire sequence of diurethane synthesis, diurethane purification and diurethane cleavage, so that deposits, which are promoted in particular by the high boiler components which are highly viscous by nature, can be substantially avoided, and also ensures good plant availability and good process yield even over the long term. Secondly, the high boiler removal downstream of the thermal cleavage reaction has the advantage that, in comparison to the customary procedure in which the high boilers are removed before the diurethane cleavage, the amount of diurethane to be converted to the vapor phase is significantly reduced, which allows capital and energy costs to be reduced.

DETAILED DESCRIPTION OF THE INVENTION

The invention provides a multistage process for continuously preparing cycloaliphatic diisocyanates, by reacting cycloaliphatic diamines with carbonic acid derivatives and alcohols to give cycloaliphatic diurethanes and subsequently freeing the cycloaliphatic diurethanes of low and medium boilers then thermally cleaving the diurethanes to give cycloaliphatic diisocyanates while by continuously discharging a portion of the cleavage residue from the cleavage apparatus and removing the high boiler components therefrom and reurethanizing the discharge purified in this way with alcohol and recycling it into the process.

The invention also provides a multistage process for continuously preparing cycloaliphatic diisocyanates of the formula (I)

OCN—R—NCO    (I)

where R is a bivalent cycloaliphatic hydrocarbon radical having from 4 to 18, preferably from 5 to 15, carbon atoms, with the proviso that the two nitrogen atoms are bonded directly to a hydrocarbon cycle and at least 3 carbon atoms are disposed between them, by reacting cycloaliphatic diamines with urea and/or urea derivatives and alcohols to give cycloaliphatic diurethanes and thermally cleaving them, wherein a) cycloaliphatic diamines of the formula (II)

$H_2N$—R—$NH_2$    (II)

where R is a bivalent cycloaliphatic hydrocarbon radical having from 4 to 18, preferably from 5 to 15, carbon atoms, with the proviso that the two nitrogen atoms are bonded directly to a hydrocarbon cycle and at least 3 carbon atoms are disposed between them, are reacted with urea and/or urea derivatives and alcohols of the formula (III)

$R^1$—OH    (III)

where $R^1$ is a radical that remains after removal of the hydroxyl group from a primary or secondary (cyclo)aliphatic alcohol having from 3 to 8 carbon atoms, in the absence or presence of dialkyl carbonates, alkyl carbamates or mixtures of dialkyl carbonates and carbamic esters, and in the absence or presence of catalysts, to give cycloaliphatic diurethanes and the ammonia formed during the reaction is simultaneously removed;

b) the alcohol, the dialkyl carbonates and/or alkyl carbamates are removed from the resulting reaction mixture, and the alcohol, and also optionally the dialkyl carbonates and/or alkyl carbamates, are recycled into the reaction stage a);

c) a removal of any high-boiling residues present in the resulting reaction mixture is fully or partially dispensed with;

d) the reaction mixture comprising the diurethanes purified by steps b) and optionally c) are continuously and thermally cleaved in the presence of a catalyst and without solvent, at temperatures of from 180 to 280° C., preferably from 200 to 260° C., and under a pressure of from 0.1 to 200 mbar, preferably from 0.2 to 100 mbar, in such a way that a portion of the reaction mixture of from 10 to 60% by weight based on the feed, preferably from 15 to 45% by weight based on the feed, is constantly discharged;

e) the cleavage products are separated by rectification into crude cycloaliphatic diisocyanate and alcohol;

f) the crude cycloaliphatic diisocyanate, purified by distillation, and the pure product fraction are isolated;

g) the bottoms discharge from d) is separated into a material-of-value stream and a waste stream, and the waste stream which is rich in high boiler components is discharged from the process and disposed of;

h) the material-of-value stream from g) is reacted with the alcohol from e) in the presence or absence of catalysts within from 1 to 150 min, preferably from 3 to 60 min, at temperatures of from 20 to 200° C., preferably from 50 to 170° C., and a pressure of from 0.5 to 20 bar, preferably from 1 to 15 bar, at a molar ratio of NCO groups to OH groups of up to 1:100, preferably 1:20 and more preferably 1:10;

i) a portion of the bottoms fraction of the purification by distillation f) is continuously discharged and conducted into the cleavage reaction d) or into the urethanization stage h);

j) optionally, the top fraction obtained in the purification by distillation f) of the crude cycloaliphatic diisocyanate is likewise recycled into the urethanization stage h);

k) the reurethanized stream from h) is recycled into stage b); or l) the reurethanized stream from h) is recycled into reaction stage a), under the condition that stage h) is carried out in the presence of catalysts selected from halides of Fe(III) and/or Cu(I).

In the process according to the invention, cycloaliphatic diisocyanates can be prepared continuously, without any significant quality or safety problems and in very good yield. Deposits, which are caused by, in particular, high boiler components which are highly viscous by nature, can be substantially prevented and good plant availability and good process yield are ensured even over long periods even when cycloaliphatic diamines of the formula (II) are used as a starting material for the continuous diisocyanate synthesis. It is a further advantage of the invention process that the amount of the diurethane to be converted to the vapor phase is reduced to a minimum and in this way reduces the necessary energy demands.

a) To prepare the monomeric cycloaliphatic diurethanes in reaction stage a), cycloaliphatic diamines of formula (II) are reacted with urea and/or urea derivatives and an alcohol of the formula (III), in some cases mixtures of such alcohols, in a molar ratio of from 1:2.01:4.0 to 1:2.2:10, preferably from 1:2.02:6 to 1:2.12:9, optionally but not preferably in the presence of dialkyl carbonates, alkyl carbamates or mixtures of dialkyl carbonates and carbamic esters, in an amount of in each case 1-10 mol % based on the diamine, in the absence or presence of catalysts, at reaction temperatures of 140-270° C., preferably 160-250° C., and under a pressure which, depending on the alcohol used, is between 2 and 80 bar, preferably 7-15 bar, for from 2 to 20 hours, preferably 4-9 hours. The reaction may be effected in a continuous stirred tank battery, but preferably in a pressure distillation reactor.

To increase the reaction rate, the cycloaliphatic diurethanes may be prepared in the presence of catalysts. Suitable catalysts are inorganic or organic compounds which contain one or more, metals or groups IA, IB, IIA, IIB, IIIA, IIIB, IVA, IVB, VA, VB, VIB, VIIB and VIIIB of the Periodic Table, defined in accordance with Handbook of Chemistry and Physics 14th Edition, published by Chemical Rubber Publishing Co. 2310 Superior Ave. N.E. Cleveland, Ohio, preferably a cation thereof, for example, halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper (II) acetate, copper(I) chloride, zinc chloride, zinc octoate, titanium tetrabutoxide, vanadium trichloride, vanadium acetylacetonate, manganese(II) acetate, iron(II) acetate, iron (II) acetate, iron oxalate, cobalt chloride, cobalt naphthenate, nickel chloride, nickel naphthenate and mixtures thereof. The catalysts may optionally also be used in the form of their hydrates or ammoniates.

The starting compounds for one embodiment f the invention process include cycloaliphatic diamines of the formula (II) mentioned above, alcohols of the formula (III) mentioned above, and also urea and/or urea derivatives which are suitable as carboxylating agents (carbonic acid derivatives), which may be reacted in the absence or presence of dialkyl carbonates, alkyl carbamates or mixtures of dialkyl carbonates and alkyl carbamates.

Suitable diamines of the formula (II) are, for example, 1,4-diaminocyclohexane, 4,4'-dicyclohexylmethanediamine, 2,4-dicyclohexylmethanediamine, 2,2'-dicyclohexylmethanediamine and isomeric cycloaliphatic diamines, and also perhydrogenated diphenylmethanediamine. As a result of the preparation, diphenylmethanediamine (MDA) occurs as an isomer mixture of 4,4'-, 2,4- and 2,2'-MDA (see, for example, DE 101 27 273, incorporated herein by reference). Perhydrogenated diphenylmethanediamine may be by fully hydrogenating MDA and is accordingly a mixture of isomeric dicyclohexylmethanediamines ($H_{12}$MDA), i.e. 4,4'-, 2,4- and 2,2'-$H_{12}$MDA. The diamines of formula (II) are preferably 4,4'-dicyclohexylmethanediamine, 2,4-dicyclohexylmethanediamine and 2,2'-dicyclohexylmethanediamine, and also any mixtures of these isomers. It will be appreciated that diamines may also be used which deviate from the formula (II). Examples include 1,3- and 1,4-diaminomethylcyclohexane, 1,6-hexanediamine, 2,2,4- or 2,4,4-trimethyl-1,6-hexanamine and 3 aminomethyl-3,5,5-trimethylcyclohexylamin However, preference is not given to using amines which deviate from the formula (II).

Suitable alcohols of the formula (III) are any aliphatic or cycloaliphatic alcohols which have a boiling point below 190° C. under atmospheric pressure. Examples include C1-C6-alkanols, for example methanol, ethanol, 1-propanol, 1-butanol, 2-butanol, 1-hexanol or cyclohexanol. The alcohol is preferably used 1-butanol.

Ammonia is released during the course of the conversion of the reaction mixture. The removal of ammonia from the reaction equilibrium has been found to be advantageous. When ammonia is discharged from the reactor, care has to be taken that the wall temperatures of the reactor and the discharge tube are above 60° C., so that deposition of ammonium carbamate, which is formed in minimal amounts from ammonia and carbon dioxide by decomposition of urea, can be prevented. It has been found to be useful, for example, to carry out the reaction in a pressure distillation reactor, in which case the reaction mixture is passed in countercurrent to alcohol vapors introduced in the bottom and in this way such intensive mixing of the liquid proceeds on the trays in a manner that they each virtually correspond to a battery stage. The vaporous mixture of alcohol and ammonia which is withdrawn at the top may, preferably under the pressure of the pressure distillation reactor and without condensing it beforehand, be passed into a distillation column in order to obtain free alcohol separated from the ammonia which may be recycled into the bottom of the pressure distillation reactor and the column. In order to prevent fouling of the reflux condenser with ammonium carbamate, an appropriate proportion of alcohol is permitted therein to set the temperature at the top to at least 60° C.

b) The excess alcohol, dialkyl carbonates, if they have been formed or are present in the reaction mixture, or alkyl carbamates or mixtures of any of these components are advantageously removed in two stages. In the first stage, the reaction mixture is decompressed from the pressure level of reaction stage a) to a pressure of 1-500 mbar, preferably 2-150 mbar, and in this way separated into gaseous vapors which contain the major amount of alcohol and also any dialkyl carbonates and/or alkyl carbamates, as a liquid effluent. In the second stage, the liquid effluent is freed of any remaining residual alcohol and also medium boilers such as dialkyl carbonates and/or alkyl carbamates by thin-film evaporation at 180-250° C., preferably 200-230° C., and a pressure of 0.1-20 mbar, preferably 1-10 mbar, so that the residue consists substantially of the monomeric polyurethane, preferably diurethane, and in some cases high-boiling oligomers.

The vapors may, preferably after distillative purification, be recycled into reaction stage a).

c) Preference is given to a process wherein any high boilers present in the reaction mixture from stage b) are not removed. However, if the separation described under g) of the bottoms discharge from stage d) is carried out only with one substream, i.e. partially, it may be advantageous to remove high boilers, as described below:

Optionally, the liquid stream from step b) which contains the monomeric diurethanes and any high-boiling oligomers obtained after the removal of low and medium boilers, may be separated, preferably with the aid of a thin-film or short-path evaporator, at a temperature of 180-260° C., preferably 200-240° C., and under a pressure of 0.01-10 mbar, preferably 0.02-5 mbar, by distillation into a material-of-value stream which contains the monomeric diurethanes and the lower-boiling by-products and a nondistillable by-product stream. The nondistillable by-product stream which contains the high-boiling components is discharged from the preparative process and is typically discarded as a residue whose material cannot be utilized.

Optionally, the stream from stage b) which contains any high-boiling oligomers, before its above-described distillative purification, may also be divided into two substreams of which one is fed directly to the deblocking reaction (see d)) and the other initially passes through the above-described high boiler removal.

d) The material-of-value stream from stage b) and optionally from stage c) which contains the monomeric diurethanes and the lower-boiling by-products is partly and continuously thermally cleaved in a suitable apparatus, without solvents in the liquid phase in the presence of catalysts at temperatures of 180-280° C., preferably 200-260° C., and under a pressure of 0.1-200 mbar, preferably 0.2-100 mbar. The degree of conversion of diurethane to diisocyanate in the apparatus for thermal cleavage may, depending on the diurethane used, be selected substantially freely and is typically within the range of 10-95% by weight, preferably 35-85% of the diurethane feed. The uncleaved proportion of the reaction mixture which contains unconverted diurethanes, high-boiling by-products and other reutilizable and nonutilizable by-products is continuously discharged. The amount of the discharge is governed, inter alia, by the desired conversion and the desired capacity of the cleavage reaction and can be easily determined experimentally. It is typically 10-60% by weight, preferably 15-45% by weight, based on the feed.

Useful catalysts for chemically cleaving the diurethanes are, for example, the aforementioned inorganic and organic compounds which catalyze urethane formation. Preference is given to using chlorides of zinc or tin, and also zinc oxides, manganese oxides, iron oxides or cobalt oxides, in which case the catalyst is metered into the stream from the purification sequence b) and optionally c) which contains substantially diurethanes, before it is fed into the cleavage, as a 0.01-25% by weight, preferably 0.05-10% by weight, solution or suspension, preferably into the alcohol which is also used for urethane preparation, in an amount of 5-400 ppm, preferably 10-100 ppm.

A suitable cleavage apparatus includes, for example, cylindrical cleavage reactors, for example tubular furnaces or preferably evaporators such as falling-film, thin-film or bulk evaporators, such as, for example, Robert evaporators, Herbert evaporators, Caddle-type evaporators, Oskar evaporators and heating cartridge evaporators.

In principle, the main concern is to keep the average residence time of isocyanate groups, which are inevitably released when the alcohol is deblocked, in the cleavage zone very low and thus to limit undesired side reactions to a minimum.

Preference is given to carrying out the cleavage in a combined cleavage and rectification column, which has an energy supply in the bottom with a falling-film evaporator, a unit in the lower third for additional energy input or for energy recovery, a unit in the upper third to remove crude diisocyanate and a condenser at the top for the reflux and the removal of pure alcohol.

e) The cleavage products which are formed in the thermal cleavage may contain, in particular alcohol, diisocyanate and partially cleaved diurethanes. The cleavage products are separated by rectification at 95-260° C., preferably 110-245° C., and a pressure of 0.5-250 mbar, preferably 1-100 mbar, into alcohol and a crude diisocyanate mixture, preferably consisting of cycloaliphatic diisocyanate, partially cleaved cycloaliphatic diisocyanate and in some cases small amounts of cycloaliphatic diurethane. This separation may be carried out, for example, in the cleavage column of the abovementioned cleavage and rectification column.

f) The crude mixture which is preferably obtained by rectification, containing cycloaliphatic diisocyanate, partially cleaved cycloaliphatic diurethane and in some cases small fractions of cycloaliphatic diurethane, is purified by distillation at a temperature of 95-260° C., preferably 110-245° C., and under a pressure of 0.5-150 mbar, preferably 1-75 mbar, and the resulting fractions are recycled into stage h) or isolated as a pure product.

g) The bottoms discharge from the cleavage stage d) is separated into a material-of-value stream and a waste stream, and the waste stream which is rich in high boiler components is discharged from the process and discarded. The two streams are separated preferably by distillation with the aid of a thin-film or short-path evaporator, at a temperature of 180-270° C., preferably 200-250° C., and under a pressure of 0.01-10 mbar, preferably 0.02-5 mbar. The material-of-value stream which contains the monomeric diurethanes and the lower-boiling by-products is obtained as the distillate. The waste stream which is rich in high-boiling components is obtained as the residue and is discharged from the preparative process and typically discarded as a nonutilizable material. Alternatively, but not preferably, the separation into material-of-value and waste material may also be effected by extraction. An example of a suitable extractant is supercritical carbon dioxide.

Optionally, the bottoms discharge may also be divided before the above-described distillative purification into two substreams one of which is fed directly to the reurethanization (see h)). The division of the two substreams may be effected in a ratio of from 99:1 to 1:99, preferably from 95:5 to 5:95.

h) The material-of-value stream from purification stage g) is combined with the alcohol from the rectification stage e), in a molar ratio of NCO groups to OH groups of up to 1:100, preferably 1:20 and more preferably 1:10, and the reaction mixture is converted, in the presence or absence of catalysts, within 1-150 min, preferably 3-60 min, at temperatures of 20-200° C., preferably 50-170° C., and a pressure of 0.5-20 bar, preferably 1-15 bar. reaction may be carried out in a continuous stirred tank reactor or a battery of stirred tanks or in a tubular reactor. Useful catalysts are in principle all catalysts which support the NCO/OH reaction. Examples include tin octoate, dibutyltin laurate, tin dichloride, zinc dichloride and triethylamine.

i) A portion of the bottoms fraction of the purifying distillation f) is continuously discharged and optionally recycled into the cleavage stage d) or into the urethanization stage h). Preference is given to recycling into the urethanization stage. The amount of the discharge is 0.1-50% by weight, preferably 0.2-25% by weight, of the feed of crude polyisocyanate into the purifying distillation stage.

j) The top fraction of the purifying distillation stage f) may be discarded or preferably recycled into the urethanization stage h). The amount of top fraction removed per unit time is 0.1-3% by weight, preferably 0.3-1% by weight, of the feed of crude polyisocyanate into the purifying distillation.

k) The stream from the urethanization stage h) is recycled into the low and medium boiler removal b).

l) Alternatively to the recycling described under k), the stream from the urethanization stage h) may also be recycled into the diurethane preparation a), as long as the urethanization was carried out in the presence of specific Lewis acid catalysts. In this context, specific catalysts refer to halides of Fe(III) or Cu(I) or mixtures thereof. Examples include iron(III) chloride, iron(III) bromide, copper(I) chloride and copper(I) bromide. The use of these specific catalysts does not in principle rule out the simultaneous use of other catalysts which serve to accelerate the urethanization. Preference is given to using the specific catalysts, i.e. the halides of Fe(III) or Cu(I) or mixtures thereof, without additional use of further catalysts.

The multistage process according to the invention for continuously preparing cycloaliphatic diisocyanates with recycling and discharge of the by-products allows, for distillable cycloaliphatic diisocyanates, a reaction which proceeds without disruption and with high selectivity over a long period. The process according to the invention is suitable in particular for preparing cycloaliphatic diisocyanates having from 4 to 18, preferably from 5 to 15, carbon atoms, such as 1,4-diisocyanatocyclohexane, 4,4'-dicyclohexylmethane diisocyanate (4,4'-$H_{12}$MDI), 2,2'-dicyclohexylmethane diisocyanate (2,2'-$H_{12}$MDI), 2,4-dicyclohexylmethane diisocyanate (2,4-$H_{12}$MDI) or else mixtures of the aforementioned isomeric dicyclohexylmethane diisocyanates, as are obtained, for example, by the conversion of perhydrogenated MDA to $H_{12}$MDI.

The cycloaliphatic diisocyanates thus prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

The invention is illustrated in detail by the examples which follow. The Examples are not intended to limit the scope of the invention.

EXAMPLES

Example 1

Preparation according to the invention of dicyclohexylmethane diisocyanate ($H_{12}$MDI) from perhydrogenated diphenylmethanediamine ($H_{12}$MDA) and urea in the presence of n-butanol—recycling of the diurethanized material into the flash stage.

Every hour, the uppermost tray of a pressure distillation reactor was charged with 280.8 g of $H_{12}$MDA, 164.0 g of urea and 599.6 g of n-butanol, and the reaction mixture was boiled at 220° C. and an average residence time of 8.5 h while continuously removing the ammonia released at 11-14 bar. The reactor effluent, together with the stream from the reurethanization, was subsequently freed of excess alcohol, low boilers and medium boilers in the flash vessel at 55 mbar with subsequent thin-film evaporation at 220° C. and 2 mbar, and the remaining 779.0 g/h of bis(4-butoxycarbonylaminocyclohexyl)methane ($H_{12}$MDU) were conducted as a melt (140° C.) into the circulation of the falling-film evaporator of the cleavage and rectification column, and the deblocking reaction was carried out at a temperature of 236° C. and a bottom pressure of 9 mbar in the presence of a steady-state concentration of tin dichloride of 15 ppm. The cleavage gases, $H_{12}$MDI and butanol, were condensed out in two condensers connected in series at 85° C. and −25° C. The resulting about 97% crude $H_{12}$MDI was fed to a purifying distillation where 319.52 g/h of $H_{12}$MDI having a purity of >99.5% were obtained, which corresponds to a yield of 91%. 227.5 g/h of butanol were obtained as the top product of the cleavage and rectification column. To maintain constant mass within the cleavage and rectification column and avoid fouling and blockages of the cleavage apparatus, a substream was continuously discharged from the circuit and separated by means of a short-path evaporator at 235° C. and a pressure of 0.04 mbar into a high boiler-rich waste stream and a material-of-value stream. The 181.3 g/h of material-of-value stream were combined together with 24.3 g/h of material separated from the bottoms of the $H_{12}$MDI purifying distillation, and also the top product from the cleavage and rectification column, and reurethanized. The reurethanized material was fed to the flash vessel together with the reactor effluent of the diurethane preparation.

Example 2

Preparation according to the invention of dicyclohexylmethane diisocyanate ($H_{12}$MDI) from perhydrogenated diphenylmethanediamine ($H_{12}$MDA) and urea in the presence of n-butanol—reurethanization in the presence of CuCl and recycling of the reurethanized Material into the diurethane synthesis.

Every hour, the uppermost tray of a pressure distillation reactor was charged with 282.1 g of $H_{12}$MDA, 164.5 g of urea and 600.8 g of n-butanol, and also the stream from the catalytic reurethanization, and the reaction mixture was boiled while continuously removing the ammonia released at 11-14 bar, 220° C. and an average residence time of 8.5 h. The reactor effluent, together with the stream from the reurethanization, was freed at 220° C. and 2 mbar of excess alcohol, low and medium boilers in the flash vessel at 55 mbar with subsequent thin-film evaporation. The remaining 778.1 g/h of bis(4-butoxycarbonylaminocyclohexyl)methane ($H_{12}$MDU) were conducted as a melt (140° C.) into the circulation of the falling-film evaporator of the cleavage and rectification column, where the deblocking reaction was carried out at a temperature of 237° C. and a bottom pressure of 9 mbar in the presence of a steady-state concentration of tin dichloride of 17 ppm. The cleavage gases, $H_{12}$MDI and butanol, were condensed out in two condensers connected in series at 85 and −25° C. The resulting about 97% crude $H_{12}$MDI was fed to a purifying distillation to obtain 318.17 g/h of $H_{12}$MDI having a purity of >99.5%, which corresponds to a yield of 90%. 228.9 g/h of butanol were obtained as the top product of the cleavage and rectification column. To maintain constant mass within the cleavage and rectification column and prevent fouling and blockages of the cleavage apparatus, a substream was continuously discharged from the circuit and separated by means of a short-path evaporator at 235° C. and a pressure of 0.04 mbar into a high boiler-rich waste stream and a material-of-value stream. The 175.6 g/h of material-of-value stream were combined together with 24.7 g/h of material separated from the bottoms of the $H_{12}$MDI purifying distillation, and also the top product from the cleavage and rectification column, and reurethanized in the presence of 100 ppm of CuCl. The reurethanized material was fed to the diurethane preparation in the pressure distillation reactor.

German application 10338511.8 filed on Aug. 22, 2003 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A process for the continuous preparation of a cycloaliphatic diisocyanate, comprising:
reacting one or more cycloaliphatic diamines with one or more carbonic acid derivatives and one or more alcohols to form a reaction mixture comprising one or more cycloaliphatic diurethanes, subsequently
separating the cycloaliphatic diurethanes from low and medium boilers present in the reaction mixture and
thermally cleaving the diurethanes to form one or more cycloaliphatic diisocyanates,
while continuously discharging a portion of a cleavage residue formed by the separating,
removing high boiler components from the discharged cleavage residue, reurethanizing the purified discharge with alcohol, and recycling the reurethanized discharge into the process.

2. A process for the continuous preparation of a cycloaliphatic diisocyanate of formula (I)

OCN—R—NCO  (I)

where R is a bivalent cycloaliphatic hydrocarbon radical having from 4 to 18 carbon atoms, the two nitrogen atoms are bonded directly to a cyclic hydrocarbon and at least 3 carbon atoms separate the nitrogen atoms, said process comprising
  a) reacting one or more cycloaliphatic diamines with at least one of urea or a urea derivative and one or more alcohols to form a reaction mixture comprising one or more cycloaliphatic diurethanes,
  wherein the cycloaliphatic diamines are of formula (II)

$H_2N-R-NH_{12}$  (II)

where R is a bivalent cycloaliphatic hydrocarbon radical having from 4 to 18 carbon atoms, the two nitrogen atoms are bonded directly to a cyclic hydrocarbon and at least 3 carbon atoms separate the nitrogen atoms, and the alcohols are of formula (III)

$R^1$—OH where $R^1$ is a radical as remains after removal of the hydroxyl group from a primary or secondary (cyclo)aliphatic alcohol having from 3 to 8 carbon atoms, wherein the reacting is carried out in the absence or presence of dialkyl carbonates, alkyl carbamates or mixtures thereof, and in the absence or presence of catalysts, to form cycloaliphatic diurethanes and the ammonia formed is simultaneously removed;
  b) removing at least one of the alcohol, the dialkyl carbonates or the alkyl carbamates from the reaction mixture, and recycling the removed alcohol into stage a) to form a purified diurethane mixture;
  c) removing some or none of any high-boiling residues present in the reaction mixture;
  d) continuously and thermally cleaving the purified diurethane mixture from b) and optionally c) without solvent in the presence of a catalyst, at a temperature of from 180 to 280° C., at a pressure of from 0.1 to 200 mbar to form a thermally cleaved mixture and a bottoms discharge, while constantly discharging a portion of the thermally cleaved mixture, wherein the amount of the thermally cleaved product discharged is from 10 to 60% by weight based on the amount of the purified diurethane mixture fed to the cleaving;
  e) separating the thermally cleaved mixture by rectification into a crude cycloaliphatic diisocyanate and an alcohol;
  f) isolating the purified crude cycloaliphatic diisocyanate, and a pure product fraction by distillation to form a bottoms fraction;
  g) separating the bottoms discharge from d) into a material-of-value stream and a waste stream, and discharging the waste stream from the process;
  h) reacting the material-of-value stream from g) with the alcohol from e) in the presence or absence of catalysts for from 1 to 150 mm, at a temperature of from 20 to 200° C,. and a pressure of from 0.5 to 20 bar, at a molar ratio of NCO groups to OH groups of up to 1:100;
  i) continuously discharging a portion of the bottoms fraction of the purification by distillation in f) and passing the discharged bottoms fraction into d) or into h);
  j) optionally, recycling a top fraction obtained in the isolating by distillation f) into stage h);
  k) recycling the reacted material-of-value stream from h) into stage b); or
  l) recycling the reacted material-of-value stream from h) into a), when h) is carried out in the presence of at least one catalyst selected from the group consisting of a halide of Fe(III) and a halide of Cu(I).

3. The process of claim 1, wherein the cycloaliphatic diamine is at least one of 4,4'-dicyclohexylmethanediamine, 2,4-dicyclohexylmethanediamine or 2,2'-dicyclohexylmethanediamine.

4. The process of claim 1, wherein the cycloaliphatic diamine is at least one of 4,4'-dicyclohexylmethanediamine or an isomeric cycloaliphatic diamine.

5. The process of claim 1, wherein the cycloaliphatic diamine is 1,4-diaminocyclohexane.

6. The process of claim 1, wherein the reacting is carried out continuously in at least one of a distillation reactor, a stirred tank reactor or a battery thereof.

7. The process of claim 1, wherein the diamine, urea and alcohol are present in a molar ratio of is from 1:2.01:4.0 to 1:2.2:10.

8. The process of claim 1, wherein the residence time of the reactants during the reacting is from 2 to 20 hours.

9. The process of claim 1, wherein the reacting is carried out in a reactor at a temperature of from 140 to 270° C. and a pressure of from 2 to 80 bar.

10. The process of claim 1, wherein the reacting is carried out at a temperature of from 160 to 250° C. and at a pressure of from 7 to 15 bar.

11. The process of claim 1, wherein the reacting is carried out in a pressure distillation reactor.

12. The process of claim 1, wherein the reactants are supplied continuously to an uppermost tray and ammonia formed during the reacting is removed by alcohol vapors introduced into the bottom of the distillation reactor.

13. The process of claim 1, wherein the alcohols have 1 to 6 carbon atoms.

14. The process of claim 1, wherein the alcohol is butanol.

15. The process of claim 1, wherein the reacting is carried out in the presence of one or more catalysts.

16. The process of claim 1, further comprising
  removing one of the alcohol, the alkylcarbonate or the dialkyl carbonate in two stages.

17. The process of claim 16, wherein a first stage the reaction mixture is decompressed from the pressure level of a) to a pressure of from 1 to 500 mbar.

18. The process of claim 16, wherein a second step a liquid effluent is freed of any residual alcohol, medium boilers, dialkyl carbonates and alkyl carbamates by thin-film evaporation at from 180° C. to 250° C. and a pressure of from 0.1 mbar to 20 mbar.

19. The process of claim 16, wherein vapors of one of the alcohol, the alkyl carbonate or the dialkylcarbonate is fed to the reacting after further distillative purification.

20. The process of claim 1, further comprising
  removing one or more high boilers from the reaction mixture at a temperature of from 180 to 260° C., preferably from 200 to 240° C., and under a pressure of from 0.01 to 10 mbar.

21. The process of claim 20, wherein the removing is carried out with the aid of a thin-film or short-path evaporator.

22. The process of claim 20, wherein one or more by-products from are discharged and discarded during removing.

23. The process of claim 20, wherein before the removing, the reaction mixture is divided into two substreams of which one substream is fed directly to the thermally cleaving.

24. The process of claim 1, wherein thermally cleaving is carried out in a combined cleavage and rectification column.

25. The process of claim 1, wherein thermally cleaving is carried out continuously at a temperature of from 180 to 280° C. and a pressure of from 0.1 to 200 mbar.

26. The process of claim 1, wherein thermally cleaving is carried out without solvent in the liquid phase.

27. The process of claim 1, wherein thermally cleaving is carried out in the presence of one or more catalysts.

28. The process of claim 1, wherein thermally cleaving is carried out in one or more tubular furnaces or evaporators.

29. The process of claim 1, wherein thermally cleaving is carried out to convert 10 to 95% by weight of the diurethane to diisocyanate.

30. The process of claim 1, wherein during thermally cleaving a portion of the reaction mixture which comprises unconverted diurethanes, high-boiling by-products and other reutilizable and nonutilizable by-products is continuously discharged.

31. The process of claim 30, wherein the amount of the discharge is from 10 to 60% by weight, based on the feed of the reaction mixture.

32. The process of claim 1, wherein the separating is carried out in a combined cleavage and rectification column.

33. The process of claim 1, carried out at a temperature of from 95 to 260° C. and a pressure of from 0.5 to 250 mbar.

34. The process of claim 1, wherein the cycloaliphatic diurethanes are separated and purified by distillation at a temperature of from 95 to 260° C. and under a pressure of from 0.5 to 150 mbar.

35. The process of claim 34, wherein a purified diurethane is isolated as a pure product or recycled.

36. The process of claim 1, carried out effected at a temperature of from 180 to 270° C. and a pressure of from 0.01 to 100 mbar.

37. The process of claim 1, further comprising
separating a material-of-value stream from the cleavage residue by distillation with the aid of a thin-film or short-path evaporator.

38. The process as claimed in claim 37, wherein separating the material-of-value is carried out by extraction.

39. The process as claimed in claim 37, further comprising
discharging a bottoms fraction before distillative purification into two substreams of which one is fed directly to the reurethanizing.

40. The process of claim 39, wherein the two substreams are divided in a ratio of from 99:1 to 1:99.

41. The process of claim 37, further comprising
reacting the material-of-value stream in a continuous stirred tank reactor or battery thereof or in a tubular reactor.

42. The process as claimed in claim 41, wherein reacting is carried out in the presence of at least one of a carboxylate, halide or tertiary amine of tin or zinc.

43. The process of claim 34, wherein a bottoms fraction is recycled to reurethanizing.

44. The process as claimed in claim 43, wherein the amount of the bottoms recycled fraction is from 0.1 to 50% by weight of the feed of crude polyisocyanate separated by distillation.

45. The process as claimed in claim 1, further comprising
separating a top fraction removed per unit time in an amount from 0.1 to 3% by weight of a feed of crude diisocyanate.

46. The process of claim 1, wherein at least one of iron(III) chloride, iron(III) bromide, copper(I) chloride and copper(I) bromide is present.

47. The process as claimed in claim 1, wherein the aliphatic diisocyanate is at least one of 1,4-diisocyanatocyclohexane, 4,4'-dicyclohexylmethane diisocyanate, 2,2'-dicyclohexylmethane diisocyanate, or 2,4'-dicyclohexylmethane diisocyanate.

48. The process according to claim 2, wherein R is a bivalent cycloaliphatic hydrocarbon radical having from 5 to 15 carbon atoms, the reaction mixture in d) is continuously and thermally cleaved at a temperature of from 200 to 260° C. and a pressure of from 0.2 to 100 mbar, and from 15 to 45% by weight of the reaction mixture is continuously discharged; the temperature at which the material-of-value stream is reacted in h) is from 50 to 170° C. for from 3 to 60 minutes at a pressure of from 1 to 15 bar and the molar ratio of the NCO groups to OH groups is up to 1:20.

49. The process of claim 48, wherein h) the ratio of NCO groups to OH groups is up to 1:10.

50. The process according to claim 8, wherein the residence time of the reactants is from 4 to 9 hours.

51. The process according to claim 18, wherein the thin-film evaporation is carried out at a temperature of from 200° C. to 230° C. at a pressure of from 1 mbar to 10 mbar.

52. The process of claim 25, wherein the thermal cleavage is carried out at a temperature of from 200 to 260° C. and a pressure of 0.2 to 10 mbar.

53. The process according to claim 28, wherein the tubular furnace or evaporator is selected from the group consisting of a falling film evaporator, a thin-film evaporator, a bulk evaporator, a Robert evaporator, a Herbert evaporator, a Caddle-type evaporator, an Oskar evaporator and a heating cartridge evaporator.

54. The process according to claim 29, wherein from 35 to 85% of the diurethane is converted to the diisocyanate.

55. The process according to claim 31, wherein the amount of discharge is from 15 to 45% by weight based on the feed.

56. The process according to claim 33, wherein the temperature is from 110 to 245° C. and the pressure is from 1 to 200 mbar.

57. The process according to claim 34, wherein the distillation is carried out at a temperature of 110 to 245° C. and at a pressure of from 1 to 75 mbar.

58. The process according to claim 40, wherein the two substreams are divided in a ratio of from 95:5 to 5:95.

59. The process according to claim 44, wherein the amount of discharge in i) is from 0.2 to 25% by weight.

60. The process according to claim 45, wherein j) the amount of the top fraction removed per unit time is from 0.3 to 1% by weight.

61. The process of claim 2, wherein the cycloaliphatic diamine is at least one of 4,4'-dicyclohexylmethanediamine, 2,4-dicyclohexylmethanediamine or 2,2'-dicyclohexylmethanediamine.

62. The process of claim 2, wherein the cycloaliphatic diamine is at least one of 4,4'-dicyclohexylmethanediamine or an isomeric cycloaliphatic diamine.

63. The process of claim 2, wherein the cycloaliphatic diamine is 1,4-diaminocyclohexane.

64. The process of claim 2, wherein a) is carried out continuously in at least one of a distillation reactor, a stirred tank reactor or a battery thereof.

65. The process of claim 2, wherein the diamine, urea and alcohol are present in a) in a molar ratio of from 1:2.01:4.0 to 1:2.2:10.

66. The process of claim 2, wherein the residence time of the reactants in a) is from 2 to 20 hours.

67. The process of claim 2, wherein a) is carried out in a reactor at from 140 to 270° C. and a pressure of from 2 to 80 bar.

68. The process of claim 2, wherein a) is carried out at a temperature of from 160 to 250° C. and a pressure of from 7 to 15 bar.

69. The process of claim 2, wherein a) is carried out in a pressure distillation reactor.

70. The process of claim 2, wherein stage a) the reactants are supplied continuously to an uppermost tray and ammonia formed during the reacting is removed by alcohol vapors introduced into the bottom of a distillation reactor.

71. The process of claim 2, wherein stage a) the alcohols have 1-6 carbon atoms.

72. The process of claim 2, wherein stage a) the alcohol is butanol.

73. The process of claim 2, wherein a) is carried out in the presence of one or more catalysts.

74. The process of claim 2, wherein b) is carried out in two stages.

75. The process of claim 74, wherein a first stage the reaction mixture is decompressed from the pressure level of a) to a pressure of from 1 to 500 mbar.

76. The process of claim 74, wherein a second step a liquid effluent is freed of any residual alcohol, medium boilers, dialkyl carbonates and alkyl carbamates by thin-film evaporation at from 180° C. to 250° C., and a pressure of from 0.1 mbar to 20 mbar.

77. The process of claim 74, wherein vapors of b) are fed into a) after further distillative purification.

78. The process of claim 2, wherein separating in stage c) is carried out at a temperature of from 180 to 260° C. and a pressure of from 0.01 to 10 mbar.

79. The process of claim 2, wherein c) is carried out with a thin-film or short-path evaporator.

80. The process of claim 2, wherein one or more by-products from c) are discharged and discarded.

81. The process of claim 2, wherein the stream in c) is divided before its distillative purification into two substreams of which one substream is fed directly to d).

82. The process of claim 2, wherein d) is carried out in a combined cleavage and rectification column.

83. The process of claim 2, wherein thermal cleavage is carried out in d) continuously at a temperature of from 180 to 280° C. and under a pressure of from 0.1 to 200 mbar.

84. The process of claim 2, wherein thermal cleavage is carried out in d) without solvent in the liquid phase.

85. The process of claim 2, wherein d) is carried out in the presence of one or more catalysts.

86. The process of claim 2, wherein d) is carried out in one or more tubular furnaces or evaporators.

87. The process of claim 2, wherein d) from 10 to 95% by weight of the diurethane is converted to diisocyanate.

88. The process of claim 2, wherein d) a portion of the reaction mixture which comprises unconverted diurethanes, high-boiling by-products and other reutilizable and nonutilizable by-products is continuously discharged.

89. The process of claim 88, wherein the amount of the discharge is from 10 to 60% by weight, based on the feed of the reaction mixture.

90. The process of claim 2, wherein e) is carried out in a combined cleavage and rectification column.

91. The process of claim 2, carried out at a temperature of from 95 to 260° C. and a pressure of from 0.5 to 250 mbar.

92. The process of claim 2, wherein f) the crude fraction obtained from stage e) is purified by distillation at a temperature of from 95 to 260° C. and a pressure of from 0.5 to 150 mbar.

93. The process of claim 92, wherein the fraction obtained in t) is isolated as a pure product or recycled into stage h).

94. The process of claim 2, wherein g) is carried out at a temperature of from 180 to 270° C. and a pressure of from 0.01 to 100 mbar.

95. The process of claim 2, wherein g) is carried out by distillation with the aid of a thin-film or short-path evaporator.

96. The process as claimed in claim 2, wherein g) is carried out by extraction.

97. The process as claimed in claim 2, wherein g) the bottoms discharge is divided before distillative purification into two substreams of which one is fed directly to h).

98. The process of claim 97, wherein the two substreams are divided in a ratio of from 99:1 to 1:99.

99. The process of claim 2, wherein h) is carried out in a continuous stirred tank reactor or battery thereof or in a tubular reactor.

100. The process as claimed in claim 2, wherein h) is carried out in the presence of one or more of a carboxylate, halide or tertiary amine of tin or zinc.

101. The process of claim 2, wherein i) the recycling is into stage g).

102. The process as claimed in claim 2, wherein i) the amount of the discharge is from 0.1 to 50% by weight of the feed of crude polyisocyanate into the purifying distillation stage.

103. The process as claimed in claim 2, wherein j) the amount of the top fraction removed per unit time is from 0.1 to 3% by weight of the feed of crude diisocyanate into the purifying distillation.

104. The process of claim 2, wherein at least one of l) iron(III) chloride, iron(III) bromide, copper(I) chloride and copper(I) bromide are present.

105. The process as claimed in claim 2, wherein the aliphatic diisocyanate is at least one of 1,4-diisocyanatocyclohexane, 4,4'-dicyclohexylmethane diisocyanate, 2,2'-dicyclohexylmethane diisocyanate, or 2,4'-dicyclohexylmethane diisocyanate.

106. The process according to claim 1, wherein R is a bivalent cycloaliphatic hydrocarbon radical having from 5 to 15 carbon atoms, the reaction mixture is continuously and thermally cleaved at a temperature of from 200 to 260° C. and a pressure of from 0.2 to 100 mbar.

107. The process according to claim 66, wherein the residence time of the reactants in a) is from 4 to 9 hours.

108. The process according to claim 76, wherein the thin-film evaporation is carried out at a temperature of from 200° C. to 230° C. at a pressure of from 1 mbar to 1 mbar.

109. The process of claim 83, wherein the thermal cleavage is carried out at a temperature of from 200 to 260° C. and a pressure of 0.2 to 10 mbar.

110. The process according to claim 86, wherein the tubular furnace or evaporator is selected from the group consisting of a falling film evaporator, a thin-film evaporator, a bulk evaporator, a Robert evaporator, a Herbert evaporator, a Caddle-type evaporator, an Oskar evaporator and a heating cartridge evaporator.

111. The process according to claim 87, wherein from 35 to 85% of the diurethane is converted to the diisocyanate.

112. The process according to claim 89, wherein the amount of discharge is from 15 to 45% by weight based on the feed.

113. The process according to claim 91, wherein the temperature is from 110 to 245° C. and the pressure is from 1 to 200 mbar.

114. The process according to claim 92, wherein the distillation is carried out at a temperature of 110 to 245° C. and at a pressure of from 1 to 75 mbar.

115. The process according to claim 98, wherein the two substreams are divided in a ratio of from 95:5 to 5:9 5.

116. The process according to claim 102, wherein the amount of discharge in i) is from 0.2 to 25% by weight.

117. The process according to claim 103, wherein j) the amount of the top fraction removed per unit time is from 0.3 to 1% by weight.

118. The process according to claim 1, wherein the cycloaliphatic diamine is at least one selected from the group consisting of 1,3-diaminomethylcyclohexane; 1,4-diaminomethylcyclohexane; hexanediamine-1,6; 2,2,4-trimethylhexanediamine-1,6; 2,4,4-trimethylhexanediamine-1,6; and 3-aminomethyl-3,5,5-trimethylcyclohexylamine.

119. The process according to claim 2, wherein the cycloaliphatic diamine is at least one selected from the group consisting of 1,3-diaminomethylcyclohexane; 1,4-diaminomethylcyclohexane; hexanediamine-1,6; 2,2,4-trimethylhexanediamine-1,6; 2,4,4-trimethylhexanediamine 1,6; and 3-aminomethyl-3,5,5-trimethylcyclohexylamine.

* * * * *